(12) United States Patent
Huang

(10) Patent No.: US 11,821,005 B2
(45) Date of Patent: Nov. 21, 2023

(54) UMBILICAL CORD MESENCHYMAL STEM CELLS (MSCS) AND CULTURE METHOD AND APPLICATION THEREOF

(71) Applicant: FOSHAN JINGZHUN JIEN HEALTH MANAGEMENT CONSULTING CO., LTD., Foshan (CN)

(72) Inventor: Jianwen Huang, Foshan (CN)

(73) Assignee: FOSHAN JINGZHUN JIEN HEALTH MANAGEMENT CONSULTING CO., LTD., Foshan (CN)

( * ) Notice: Subject to any disclaimer, the term of this patent is extended or adjusted under 35 U.S.C. 154(b) by 576 days.

(21) Appl. No.: 16/862,510

(22) Filed: Apr. 29, 2020

(65) Prior Publication Data

US 2020/0377859 A1 Dec. 3, 2020

(30) Foreign Application Priority Data

May 27, 2019 (CN) .......................... 201910445831.2

(51) Int. Cl.
*C12N 5/0775* (2010.01)
*A61K 35/51* (2015.01)
*A61K 9/00* (2006.01)

(52) U.S. Cl.
CPC .......... *C12N 5/0665* (2013.01); *A61K 9/0019* (2013.01); *A61K 35/51* (2013.01); *C12N 2500/02* (2013.01); *C12N 2500/30* (2013.01); *C12N 2500/90* (2013.01)

(58) Field of Classification Search
CPC ............. C12N 5/0665; C12N 2500/30; C12N 2500/76; C12N 2501/999; A61K 35/51
See application file for complete search history.

*Primary Examiner* — Taeyoon Kim
(74) *Attorney, Agent, or Firm* — Daniel M. Cohn; Howard M. Cohn

(57) ABSTRACT

An umbilical cord mesenchymal stem cells (MSCs) and culture method and application thereof, which comprises an MSCs culture step comprising the following substeps: primary culture: culturing Wharton's jelly of an umbilical cord in a serum-free medium under a hypoxic condition; subculture: collecting P1 primary cells to prepare a single cell suspension which is centrifuged to obtain a cell pellet; adding a serum-free medium to the cell pellet, culturing under a hypoxic condition until passage, and continuously culturing up to P2-P3; adding a ligustrazine hydrochloride and a Shenmai injection during each subculture, digesting cells grown to a predetermined fusion degree, and collecting the cells cultured to P6; phenotypic test: testing the phenotype of the collected cells for later use. An MSCs preparation cultured by the method reduces easy aggregation of stem cells, thus avoiding cell adhesion, rouleau formation of red cells and cell cluster embolism after intravenous infusion into human bodies.

12 Claims, 4 Drawing Sheets

UMBILICAL CORD MESENCHYMAL STEM CELLS (MSCS) AND CULTURE METHOD AND APPLICATION THEREOF

TECHNICAL FIELD

The invention relates to the field of biomedical technology, in particular to an umbilical cord mesenchymal stem cells (MSCs) and a culture method and application thereof.

BACKGROUND

According to the forecast of the World Health Organization, non-communicable diseases will account for 79% of the causes of deaths in China by 2020, with cardiovascular diseases taking the first place. As cardiomyocytes are terminal differentiated cells, necrotic cells can not be regenerated but can only be replaced by scar formation, resulting in the loss of myocardial contractile function and death due to intractable heart failure. According to the case survey of 50 Grade-A Tertiary Hospitals in China, the hospitalization rate of heart failure accounts for 20% of cardiovascular diseases in the same period, but the mortality rate accounts for 40%. The five-year survival rate is similar to that of malignant tumors. Clinical drugs, interventional therapy and surgical treatment are passive and remedial treatment which cannot replace necrotic myocardium. However, heart transplantation is difficult to promote in clinic because of donor difficulties. Meanwhile, stem cell transplantation provides a new treatment method.

Umbilical cord mesenchymal stem cells (MSCs) is a kind of pluripotent stem cells existing in neonatal umbilical cord tissue, which can differentiate into many kinds of tissue cells and has a broad clinical application prospect. As mesoderm-derived stem cells with a multilineage differentiation potential, MSCs can differentiate into multiple tissue cells, such as fibroblasts, adipocytes, vascular epithelial cells, chondrocytes, osteocytes, muscle cells, neurocytes, hepatocytes, cardiomyocytes, islet p cells and endothelial cells under specific inducing conditions in vitro, and still has a multilineage differentiation potential after continuous subculture and cryopreservation. With low immunogenicity, MSCs, autologous or allogeneic, generally does not induce an immune response in the host. MSCs has the characteristic of aggregation to degenerated, ischemia or damaged tissues, which is medically known as a homing phenomenon. MSCs exists in umbilical cords, adult mesenchymal tissues, bone marrows and deciduous teeth. Among them, bone mesenchymal stem cells (BMSC) account for only $1/10000$-$100000$ of the total number of bone marrow nucleated cells. MSCs is relatively pure and abundant in placenta and umbilical cords. Domestic and foreign scholars have induced differentiation of MSCs with 5-azacitidine (5-aza) after cell passage during in vitro culture, and found cardiomyocyte-like ultrastructures, myocardial specific gene expression and sustained action potentials, which indicates that the scholars have successfully induced cardiomyocytes. Some other scholars have injected MSCs directly into autologous myocardial tissues, and found cardiomyocyte-like cells and cardiomyocyte specific markers with troponin T and myosin heavy chains, which indicates that MSCs can be induced to differentiate into cardiomyocytes under microenvironment conditions in vivo microenvironment.

Current opinions on culturing conditions of MSCs are different. The culture conditions such as oxygen density and humidity of the incubators, the selection of medium, the type and concentration of serum, the time and frequency of the first liquid change and the amount of liquid and other factors will affect the proliferation of MSCs. A common in vitro culture system of MSCs is to culture MSCs in a complete medium with normal oxygen concentration, and the complete medium usually contains fetal bovine serum.

However, MSCs can highly express CXCR4 (chemokine receptor 4), however, due to the different viability potential of mesenchymal seed stem cells extracted from different ages and different tissue sources, and the different culture methods also greatly affected the characteristics of MSCs, MSCs can express CXCR4 (chemokine receptor 4), but the expression ability of CXCR4 decreased significantly after normoxic culture. The culture method with fetal bovine serum may be detrimental to the clinical application of stem cell therapy due to serum sickness caused by residual animal serum after infusion of MSCs into human bodies. Moreover, only a few of MSCs cultured in vitro for intravenous infusion can be implanted into injured parts of human bodies or animals while most of the cells remain in microvessels (especially in the lungs) and die. Meanwhile, MSCs has the characteristics of adherent growth, and MSCs often aggregate during in vitro culture. Therefore, stem cell adhesion, aggregation and cell cluster embolism may occur after intravenous infusion into human bodies.

For the above reasons, MSCs cultured in vitro will bring adverse reactions in the treatment of diseases and affect the efficacy, hindering the clinical treatment of stem cells.

SUMMARY OF THE INVENTION

On this basis, it is necessary to provide a MSCs and its culture method and application thereof in response to solve the above problems. MSCs cultured by the method reduces aggregation of stem cells, thus avoiding stem cell adhesion, rouleau formation of red cells and cell cluster embolism after intravenous infusion into human bodies.

A culture method of MSCs, characterized by comprising an MSCs culture step which comprises the following sub-steps:
  primary culture: culturing Wharton's jelly of umbilical cords in serum-free medium under a hypoxic condition until it reaches the subculture standard;
  subculture: collecting P1 primary cells obtained in said primary culture step and removing residual medium to prepare a single cell suspension which is centrifuged to obtain a cell pellet; adding a serum-free medium to the cell pellet, culturing under a hypoxic condition until passage, and continuously culturing to P2-P3; adding ligustrazine hydrochloride and Shenmai injection during each subsequent subculture, digesting and collecting cells grown to a predetermined fusion degree;
  phenotypic test: testing the phenotype of the cells collected in said subculture step, and taking cells with CD31-negative, HLA-DR-negative, CD34-negative, CD45-negative, CD44-positive, CD73-positive, CD90-positive and CD105-positive as required MSCs for later use.

In practice, only a few of MSCs cultured in vitro for intravenous infusion can be implanted into injured parts of receptors while most of the cells remain in capillaries and die. In addition, aggregation of MSCs occurs frequently during in vitro culture, and adhesion, aggregation and cell cluster embolism may occur in intravenous infusion, which brings adverse reactions to the application of MSCs cultured in vitro to the treatment of diseases and affects the efficacy, hindering the clinical application of stem cells. On this basis, a traditional Chinese medicine Shenmai injection with the functions of nourishing qi to stop collapse, nourishing Yin and generating body fluid and a hydrochloride of ligustrazine which is an active ingredient of traditional Chinese medicine *Ligusticum wallichii* with the characteristics of activating blood circulation to remove blood stasis are added to a cell culture solution. Ginsenoside contained therein can promote the synthesis of DNA and RNA of cells, increase the AMP value in plasma, inhibit platelet aggregation, reduce fibrinogen content of plasma, remove microthrombosis and improve the microenvironment of stem cells. Radix Ophiopogonis can stabilize cytomembrane. The ligustrazine hydrochloride has the effects of increasing the surface charges of cells and platelets, inhibiting platelet aggregation and thrombosis, and improving hemorheological properties. The ligustrazine hydrochloride gives full play to cytoprotection through the combined action of a plurality of active ingredients such as anti-oxidation, anti-inflammation and apoptosis inhibition so as to reduce MSCs agglomeration, adhesion and aggregation in intravenous infusion, cell cluster embolism and rouleau formation of red cells, which greatly improves the application of the MSCs in the prevention and treatment of myocardial infarction.

Further, the concentration of ligustrazine hydrochloride added is 40-80 mg/L and said Shenmai injection added is 0.5% by volume in said subculture step. The Shenmai injection can be directly injected into human body.

Further, in the MSC culture step, the hypoxic condition is as follows: culturing in a carbon dioxide incubator with an oxygen concentration of 3-10%, preferably 5%; and the serum-free medium is selected from a mesenchymal stem cell serum-free medium or a medium obtained by adding cytokines to a DMEM, F12, DMEM/F12 or RPM11640 basal medium. The mesenchymal stem cell serum-free medium is preferably a product of Yocon Biology.

Traditional MSCs is commonly cultured under normal oxygen, and the implantation rate of MSCs is low. However, the culture of MSCs under a hypoxic condition (3-10% oxygen concentration, preferably 5%) can improve the ability of MSCs cultured in vitro to resist intravascular hypoxic environment. It has been found that the proliferation and colony formation ability of MSCs cultured under a hypoxic condition are enhanced, and the implantation rate of MSCs in vivo after infusion into human bodies is increased, thus improving the efficacy of the MSCs. In addition, fetal bovine serum is more or less used in traditional MSCs culture systems. While the culture technique using a non-serum medium in the invention can avoid serum sickness caused by residual animal serum after infusion of an MSCs preparation into human bodies.

Further, the standard of passage is that the cells grow to a fusion degree of 80-90% in the primary culture step;

In the subculture step, the ligustrazine hydrochloride and the Shenmai injection are added and then continue to be cultured and subcultured to P4-P6.

Further, before the MSCs culture step, the MSCs preparation step also includes the following MSCs preparation step; after the MSCs culture step, the quality control step also includes the following steps: preparation of MSCs: collecting umbilical cord tissues obtained by caesarean sections, transporting the tissues under refrigeration, making sure that the samples are not exposed to high-energy radiation, cleaning and stripping blood vessels in the tissues to obtain Wharton's jelly from the tissues;

quality control: identifying the cells and testing the purity, cell growth activity, bacteria and mycoplasma, endotoxin, exogenous pathogenic factors, abnormal immune response, tumorigenicity and/or residual volume of ingredients added of the obtained required MSCs.

Further, the MSCs preparation step also includes the following donor screening steps:
1) donors were tested for fulminant infectious diseases, including HIV, hepatitis B virus, hepatitis C virus, *Treponema pallidum*, cytomegalovirus, EB virus and human T-cell lymphotropic virus before sample collection, and donors not infected with the fulminant infectious diseases may be eligible;
2) donors are subject to a DNA test for genetic disorders, including achondroplasia, congenital deafness, vitamin D-resistant rickets, phenylketonuria, hemophilia, progressive muscular dystrophy and glucose-6-phosphate dehydrogenase deficiency before sample collection, and donors may be eligible if all the infectious diseases are negative;
3) donors have not traveled to or stayed in epidemic areas within 3 months before sample collection;

those who meet all the criteria are eligible donors.

In the donor screening, in order to prevent adverse effects of congenital genetic disease susceptibility genes carried with the cultured umbilical cord MSCs on patients after reinfusion, the quality of cell products is strictly controlled in the invention from raw materials, semi-finished products and products.

Further, the invention also discloses a stem cell cultured by the culture method of MSCs.

Further, the invention also discloses an MSCs injection comprising the MSCs, heparin sodium, a compound amino acid and pharmaceutically acceptable adjuvants.

The MSCs of the invention can be prepared into a compound preparation for preventing and treating human myocardial infarction and severe lesions and stenosis in three coronary arteries.

Further, the compound amino acid comprises L-isoleucine, L-arginine, L-leucine, L-aspartic acid, L-lysine, L-cysteine, L-glutamic acid, L-methionine, L-histidine, L-phenylalanine, L-proline, L-threonine, L-serine, L-tryptophan, L-tyrosine, L-valine, L-glycine and L-alanine; and the concentration of the compound amino acid is 10±2 g/100 ml. A compound amino acid injection 18AA-III can be directly used as the compound amino acid.

An amino acid mixture prepared with the above ratio can be directly injected into human blood to supplement nutrition and partially replace plasma, thus improving disease resistance of patients with trauma, burns and postoperative patients, and promoting the rehabilitation of patients with myocardial infarction.

Furthermore, the concentration of the MSCs is $(0.5-1.5) \times 10^9$ cells/100 ml.

The invention also discloses the application of the umbilical cord MSCs in preparing drugs for prevention and treatment of myocardial infarction.

Compared with the prior art, the invention has the following beneficial effects:

In the culture method of the umbilical cord MSCs of the invention, the culture of MSCs under hypoxic non-serum conditions can enhance the proliferation and colony formation ability of MSCs cultured in vitro, enhance the adaptability of hypoxic growth in blood vessels, improve the implantation rate of the MSCs in vivo after infusion into human bodies, and avoid serum sickness possibly caused by residual animal serum after infusion of the MSCs into human bodies. In addition, the traditional Chinese medicine Shenmai injection with the functions of nourishing qi to stop collapse, nourishing Yin and generating body fluid and a ligustrazine hydrochloride preparation of traditional Chinese medicine *Ligusticum wallichii* with the characteristics of activating blood circulation to remove blood stasis are innovatively added to a cell culture solution. With stable properties, the ligustrazine hydrochloride added can reduce aggregation of the MSCs, and effectively prevent the occurrence of adhesion, aggregation, rouleau formation of red cells and cell cluster embolism in intravenous infusion.

In addition, sampling is very strict, and all donors and umbilical cords used for manufacturing are subject to a DNA test for severe genetic diseases for the first time in the invention so as to ensure the traceability of the produced MSCs and eliminate adverse effects of carried congenital genetic disease susceptibility genes on patients after reinfusion.

In the invention, the MSCs cultured under hypoxic non-serum conditions are prepared into a compound preparation. The compound preparation is prepared from 18 L-amino acids prepared in advance when in use, hypoxic non-serum MSCs, an MSCs composite liquid and heparin-containing physiological saline infused afterwards. The MSCs preparation cultured by the method improves the therapeutic effect of preventing and treating human myocardial infarction and severe lesions and stenosis in three coronary arteries.

DETAILED DESCRIPTION OF THE PREFERRED EMBODIMENTS

Figure 1:
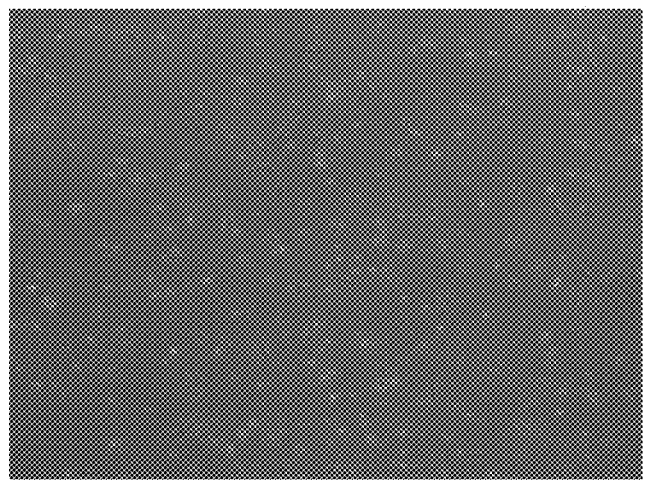
FIG. 1 is a cell graph of P3 cells in Example 1 on Day 1 after a Shenmai injection is added.
Figure 2:
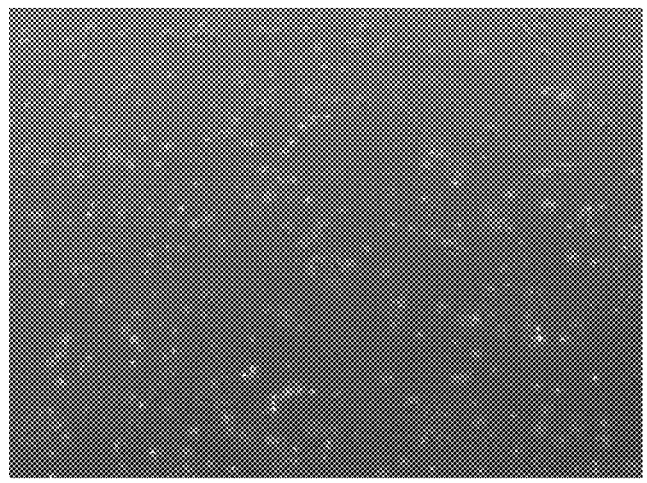
FIG. 2 is a cell graph of P3 cells in Example 1 on Day 1 after a ligustrazine hydrochloride is added.
Figure 3:
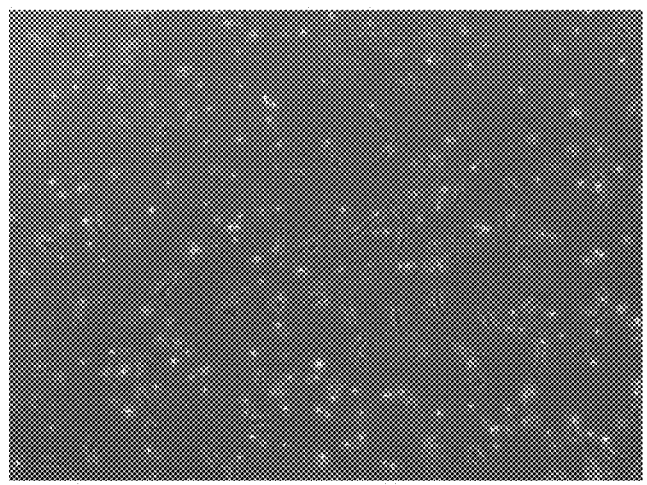
FIG. 3 is a cell graph of P3 cells in Example 1 on Day 1 after the ligustrazine hydrochloride and the Shenmai injection are added.
Figure 4:
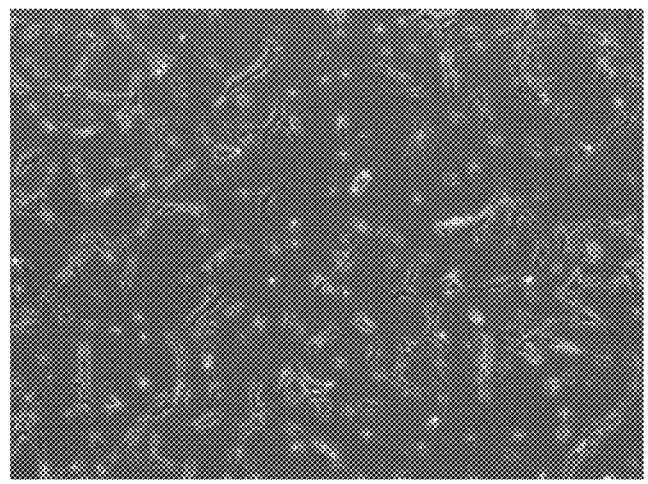
FIG. 4 is a cell graph of P4 cells in Example 1 on Day 1 after the Shenmai injection is added.
Figure 5:
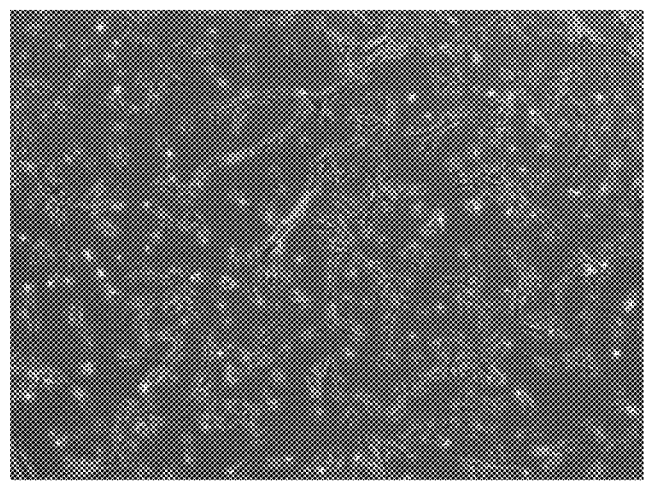
FIG. 5 is a cell graph of P4 cells in Example 1 on Day 1 after the ligustrazine hydrochloride is added.
Figure 6:
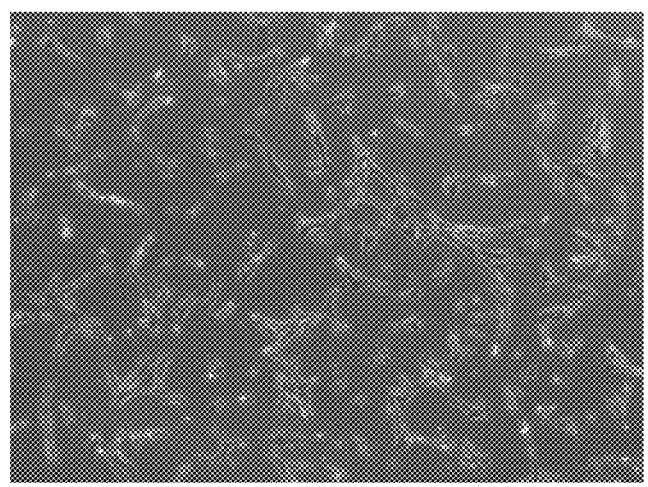
FIG. 6 is a cell graph of P4 cells in Example 1 on Day 1 after the ligustrazine hydrochloride and the Shenmai injection are added.
Figure 7:
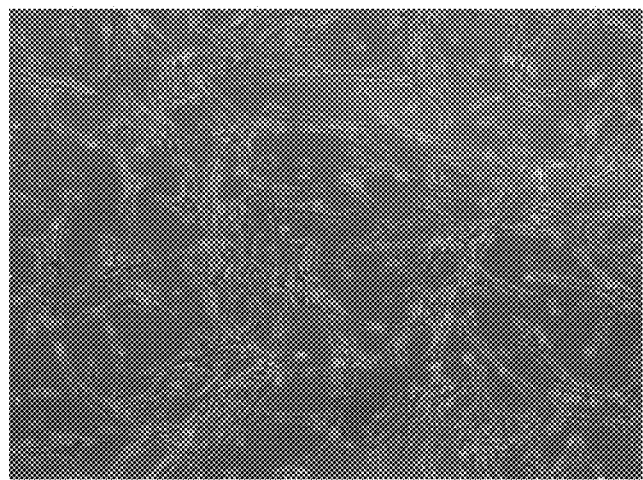
FIG. 7 is a cell graph of P5 cells in Example 1 on Day 1 after the Shenmai injection is added.
Figure 8:
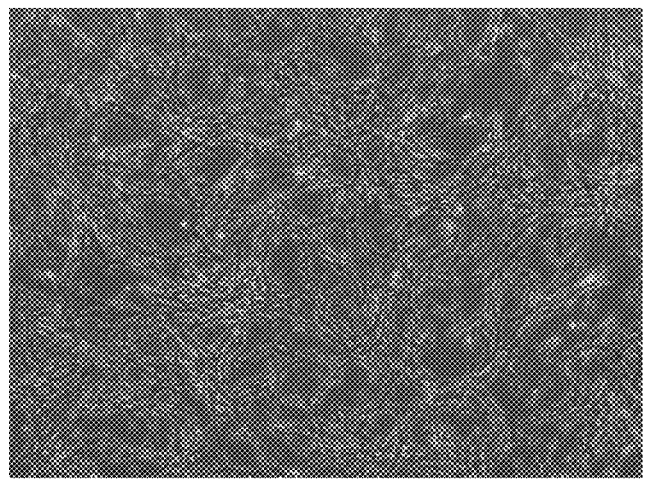
FIG. 8 is a cell graph of P5 cells in Example 1 on Day 1 after the ligustrazine hydrochloride is added.
Figure 9:
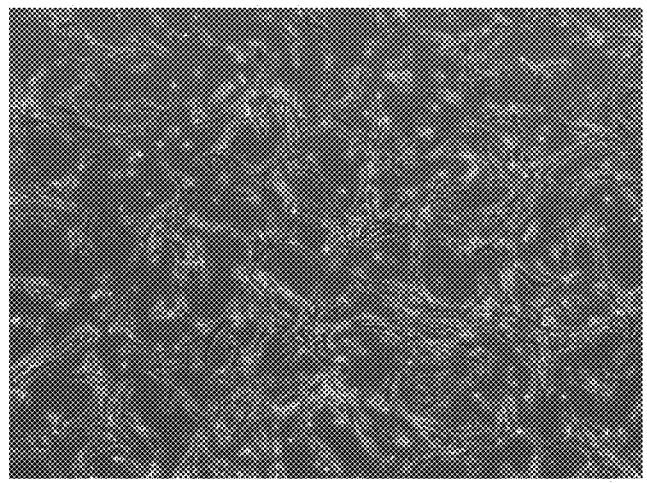
FIG. 9 is a cell graph of P5 cells in Example 1 on Day 1 after the ligustrazine hydrochloride and the Shenmai injection are added.

The invention is described more fully hereinafter with reference to the accompanying drawings for understanding the invention, in which preferred embodiments of the invention are shown. The invention may, however, be embodied in many different forms and should not be construed as limited to the embodiments set forth herein. Rather, these embodiments are provided so that the disclosure of the invention will be thorough and complete.

Unless otherwise defined, all technical and scientific terms used herein have the same meaning as commonly understood by one of ordinary skill in the art to which the invention pertains. The terminology used herein in the Specification of the invention is for the purpose of describing particular embodiments only and is not intended to limit the invention. Also, as used herein, the term "and/or" includes any and all combinations of one or more associated listed items.

Example 1

An MSC, which was cultured by the following method:

I. Donor Screening

1. Blood of donors was drawn for testing for fulminant infectious diseases within one month before sample collection, including but not limited to human immunodeficiency virus (HIV), hepatitis B virus (HBV), hepatitis C virus (HCV), *Treponema pallidum* (TP), cytomegalovirus (CMV), EB virus and human T-cell lymphotropic virus (HLTV). Donors carrying pathogen (including those previously infected with *Treponema pallidum*) of any of the seven infectious diseases were excluded.

2. Blood of donors was drawn for a DNA test for severe genetic diseases within one month before sample collection, including but not limited to achondroplasia, congenital deafness, vitamin D-resistant rickets, phenylketonuria, hemophilia, progressive muscular dystrophy and glucose-6-phosphate dehydrogenase (G-6-PD) deficiency (favism). As the DNA test for severe genetic diseases is an important basis for the traceability of important links in cell culture sampling, donors with positive test results were excluded.

3. Donors did not travel to or stay in epidemic areas over the past 3 months.

Those who meet all the criteria are eligible donors.

II. Preparation of MSCs

1. Sample Collection

The donors who passed the screening signed a sample donation agreement. After full-term pregnancy, donors delivered by caesarean sections, placenta and umbilical cord tissues were refrigerated (2-8° C.) within 48 hours and transported to a laboratory in special sterile sampling bags sealed with a proper amount of refrigerated tissue preservation solution. During transport, the sampling bags were kept unbroken without content leakage, and samples were kept unexposed to X ray, γ ray and other high-energy ray irradiation.

It is very important to use umbilical cords obtained by caesarean sections as the samples because umbilical cords from natural delivery will produce various microbial contamination when passing through birth canals, affecting the quality of MSCs.

2. Sample Preparation 2.1 The samples transported to the laboratory were unbagged in a sterile biosafety cabinet, and the umbilical cord tissues were cleaned off blood stains on the surfaces with a pre-cold cleaning solution.

2.2 The umbilical cords were cut into 2-3 cm segments and washed several times again.

2.3 The arteries and veins in the umbilical cord tissues were stripped with tissue forceps, then Wharton's jelly was stripped from the umbilical cords and placed in a precooled tissue cleaning solution, and epidermal tissues could not be mixed in the Wharton's jelly.

III. MSCs Culture

1. Primary Culture 1.1 All the stripped Wharton's jelly was cleaned with a precooled tissue preservation solution several times and then placed in a 50 ml centrifugal tube, and the tissues were cut to a volume of not greater than 3×3×3 mm³.

1.2 A proper amount of serum-free medium (containing 100 U/ml of penicillin/streptomycin) (serum-free medium for MSCs of Yocon Biology) was added to the cut tissues to obtain a culture solution, then 10 ml of the culture solution was inoculated in each T75 culture flask on average, and the culture flask was placed in a 37° C. constant temperature carbon dioxide incubator for normal culture under a hypoxic condition with oxygen concentration of 3-10%, preferably 5%.

1.3 All medium was changed on Day 5th of the primary culture, and half of medium was changed 3 days later. Under normal circumstances, some cells migrated out of tissue masses on Day 10 and grew to a fusion degree of 90% on Day 15th, which met the standard of passage.

2. Subculture 2.1 The special medium in the culture flask for passage was collected and centrifuged at 3000 rpm for 10 minutes, and a supernatant was collected for later use.

2.2 Primary cells in the culture flask were washed twice with physiological saline to remove residual medium.

2.3 Then 3 ml of 0.05% trypsin was added to digest the cells and the culture flask was tapped to allow all adherent cells to fall off, then 5 ml of special medium after centrifugation was added to terminate pancreatic enzymes and the cells were gently blown to obtain single cell suspension.

2.4 After the cell suspension was collected, the culture flask was washed twice with physiological saline, then all liquid was collected and filtered through a 100 μm filter screen to remove undigested tissue masses.

2.5 The filtered single cell suspension was centrifuged at 1300 rpm for 6 min to remove the supernatant.

2.6 To the cell pellet, 15 ml of physiological saline was added to resuscitate the cells. After mixing, a small amount of liquid was taken for counting, and the mixture was centrifuged again at 1300 rpm for 6 min to remove the supernatant.

2.7 Every 500 ml of a mixture of the cell pellet and a serum-free medium (antibiotic-free) was prepared into a cell suspension. The serum-free medium was a serum-free medium for mesenchymal stem cells of Yocon Biology, or a medium obtained by adding cytokines to a DMEM, F12, DMEM/F12 or RPMI1640 basal medium of GIBCO. According to the cell count result, the cell suspension was inoculated in a T175 culture flask at a density of 10000/cm², and the culture flask was placed in a 37° C. constant temperature carbon dioxide incubator for normal culture under a hypoxic condition with oxygen concentration of 3-10%, preferably 5%.

2.8 The cells grown to a fusion degree of 90% (about 3 days) were subcultured again to P2.

2.9 A ligustrazine hydrochloride (GYZZ H20041175 injection of Harbin Medisan Pharmaceutical Co., Ltd., which follows the Second Supplement to the National Standard and can be directly injected into human bodies) and a Shenmai injection (GYZZ Z63021721 of Yunnan Phytopharmaceutical Co., Ltd., which follows the National Drug Standard (Amendment) WS3-B-3428-98-2010 and can be directly injected into human bodies) were added to P3-P5 cells respectively. The concentration of the ligustrazine hydrochloride was 40-80 mg/L and the Shenmai injection was 0.5% by volume. After culture for 24 hours, change the medium and culture for another one week, the cells grown to a fusion degree of 80-90% were collected and digested for tests. The products obtained in the steps are biodetected to eliminate etiological contamination.

The cells were divided into three groups: a. only the Shenmai injection was added; b. only the ligustrazine hydrochloride was added; and c. both the Shenmai injection and the ligustrazine hydrochloride were added for comparison. The results were shown in FIG. 1 to FIG. 9, it can be seen from the figures that the agglomeration of the cells was improved to some extent when the ligustrazine hydrochloride or the Shenmai injection was added, but the best effect was obtained when both the ligustrazine hydrochloride and the Shenmai injection were added at the same time.

3. Phenotypic Test 3.1 The cells collected were subject to a phenotypic test, and cells with CD31-negative, HLA-DR-negative, CD34-negative, CD45-negative, CD44-positive, CD73-positive, CD90-positive and CD105-positive were taken as qualified required MSCs.

3.2 The qualified required MSCs were resuspended in a special freezing medium at a density of $1\times10^7$/ml according to the count result. Single cells suspended in the freezing medium were added to freezing tubes (1 ml each) and labeled, with label information, including but not limited to cell type, cell number, passage number of frozen cells, cell count of frozen cells in each tube and freezing date. The freezing tubes were sealed with a sealing film, then slowly cooled to −90° C. by a programmed cooling instrument, and directly placed in liquid nitrogen at −205° C. to −185° C. (preferably −196° C.) for long-term storage after program cooling.

IV. Quality Control

The quality control of the umbilical cord MSCs in the example follows the quality testing standards for stem cell preparations in the *Guiding Principles for Quality Control aid Preclinical Research of Stem Cell Preparations* (*Trial*) *issued by China Food and Drug Administration in* 2015.

1. Cell identification and purity test: cell morphology, multilineage differentiation potentials and surface markers were used to test and identify whether the cultured cells were MSCs and their purity. The surface markers included positive indicators (>95%): CD44, CD73, CD90, CD105, and negative indicators (<2%): CD34, CD45, HLA-DR, multilineage differentiation potentials.

2. Cell growth activity: cell growth activity was tested by CCK8, cell doubling time, cell cycle, clone forming efficiency, telomerase activity and telomere length, and cell senescence was tested by D galactosidase.

3. Test of bacteria and mycoplasma: bacterial, fungal and mycoplasma contamination of the samples was tested in accordance with procedures for testing sterility and mycoplasma of biological preparations in Chinese Pharmacopoeia (2015 Edition).

4. Endotoxin test: endotoxin of the samples was tested in accordance with procedures for testing endotoxin in Chinese Pharmacopoeia (2015 Edition).

5. Test of exogenous pathogenic factors: DNA test for pathogens of donor-derived fulminant infectious diseases, including human immunodeficiency virus (HIV), hepatitis B virus (HBV), hepatitis C virus (HCV), *Treponema pallidum* (TP), cytomegalovirus (CMV), EB virus and human T-cell lymphotropic virus (HLTV); test of bovine-derived specific viruses, including mad cow disease and aftosa; and swine-derived specific viruses, including porcine parvovirus.

6. Abnormal immune response: effects of the MSC on the proliferation of human total lymphocytes and specific lymphocyte subsets (including CD4+T cells, CD8+T cells, B cells, NK cells) and the secretion of associated cytokines (including INF-γ, TNF-α, IL-4, IL-6 and IL-10) were tested.

7. Tumorigenicity test: the tumorigenicity of cells was tested by implanting high-dose MSCs into immunodeficient animals to observe tumorigenesis.

8. Test of residue of added ingredients: the residual volume of ingredients (including bovine serum albumin (BSA), antibiotics, specific cytokines and phenol red) that affect the safety of stem cell preparations during preparation in the final product was tested.

Example 2

An MSCs injection, which was obtained by the following method.

1. Preparatory Work 1.1 Water bath was reheated to stabilize the water temperature at 37° C.

1.2 A biosafety cabinet was subject to ultraviolet disinfection and ventilation 30 min in advance.

1.3 Physiological saline was provided according to the cell count of thawed cells and added to a centrifuge tube and the volume of the physiological saline was at least 10 times than that of all freezing medium.

2. Information Checking

Frozen cells were taken out of a liquid nitrogen tank according to the predetermined demand, and key information such as cell type, cell code, cell count and cell passage number was carefully checked to prevent errors.

3. The frozen cells taken out of the liquid nitrogen tank were immediately placed in the reheated water bath for thawing for 2 min until the freezing medium completely thawed, and the frozen cells were constantly shaken while ensuring that the freezing tube mouth did not contact with the water in the water bath.

4. Thawed freezing tubes were taken out and transferred to a biosafety cabinet after the tube bodies were wiped with 75% alcohol.

5. The cell suspension in the freezing tubes was completely sucked into a centrifuge tube containing physiological saline, and the tubes were washed with physiological saline for 2-3 times, then all the liquid was transferred into the centrifuge tube and mixed.

6. The cell suspension was centrifuged at 1300 rpm for 6 min to remove the supernatant, then the cells were resuspended in fresh physiological saline, centrifuged and washed repeatedly for 3 times.

7. After washing, 100 ml physiological saline was added to prepare a group of composite preparations.

The number of cells containing hypoxic MSCs in each group of composite preparations is $(0.5\text{-}1.5) \times 10^9$, the physiological saline in each group of composite preparations contained 10-20 Um low molecular weight heparin sodium, and each group of composite preparations contains 18 L-compound amino acids.

The compound amino acid injection is composed of 18 amino acids, including L-isoleucine, L-arginine, L-leucine, L-aspartic acid, L-lysine, L-cysteine, L-glutamic acid, L-methionine, L-histidine, L-phenylalanine, L-proline, L-threonine, L-serine, L-tryptophan, L-tyrosine, L-valine, L-glycine and L-alanine, and contained 10±2 g amino acids per 100 ml (said compound amino acid injection was a compound amino acid injection 18AA-III that was commercially available).

The cells were resuspended and filtered through a 40 μm filter screen to remove agglomerated cells to obtain a single cell suspension.

8. A small amount of cell suspension was taken to count the cells to obtain the total cell count and cell viability so as to ensure that the cell count and viability were not lower than predetermined requirements.

9. The cell suspension was loaded in a special cell reinfusion bags (bottles) and completely sealed. Before the cell suspension was loaded in the reinfusion bags, samples were taken for endotoxin test, with 1 ml of each sample reserved.

10. The endotoxin content of the cell suspension to be reinfused was tested according to standard operating procedures of limulus reagent gel method, and the endotoxin content of the reinfused cell suspension was lower than 0.5 EU/ml according to the requirements of Chinese Pharmacopoeia (2015 Edition).

11. The products passing the endotoxin test were released, otherwise the products would be destroyed centrally and the causes would be investigated.

12. The reserved cell suspension was labeled and stored at −20° C. for at least one year, with label information including but not limited to product number, cell type, cell number, date of manufacture and responsible person.

13. Released products were sent out of the laboratory after carefully checking of the product information by a quality inspector, and transported to reinfusion sites within 4 hours under refrigeration (2-8° C.) for reinfusion. During transport, the cell suspension was kept unexposed to X-ray or γ-ray and other high energy ray irradiation.

Example 3

An application of MSCs injection in the treatment of myocardial infarction.

The umbilical cord MSCs preparation of the invention has extensive applications. At present, we have prepared the MSCs of Example 1 into a compound preparation as shown in Example 2 and applied the compound preparation to the treatment of patients with myocardial infarction to observe the efficacy.

1. The morphology of peripheral blood cells was observed under microscope.

1. Method

The peripheral blood in the control group (MSCs cultured without ligustrazine hydrochloride and Shenmai injection) and in the treatment group (the compound preparation of Example 2) were observed under microscope.

2. Results

Figure 10:
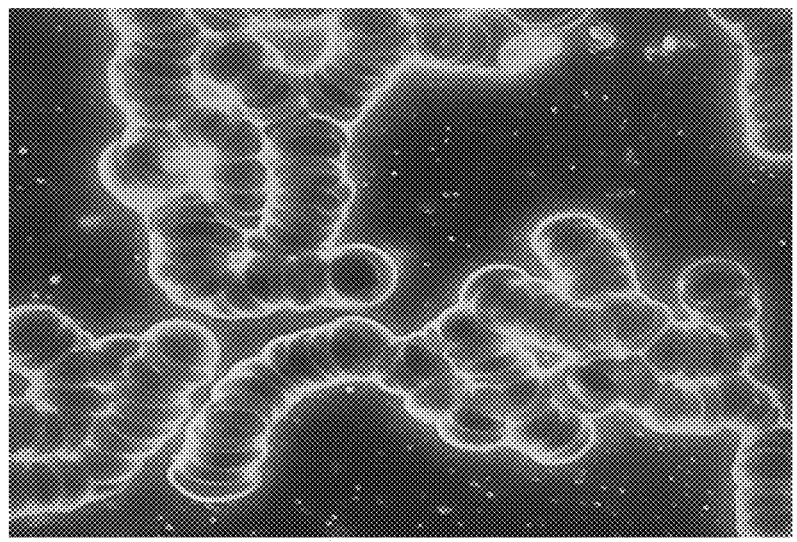
FIG. 10 is a cell graph of peripheral blood of the control group in Example 3.
Figure 11:
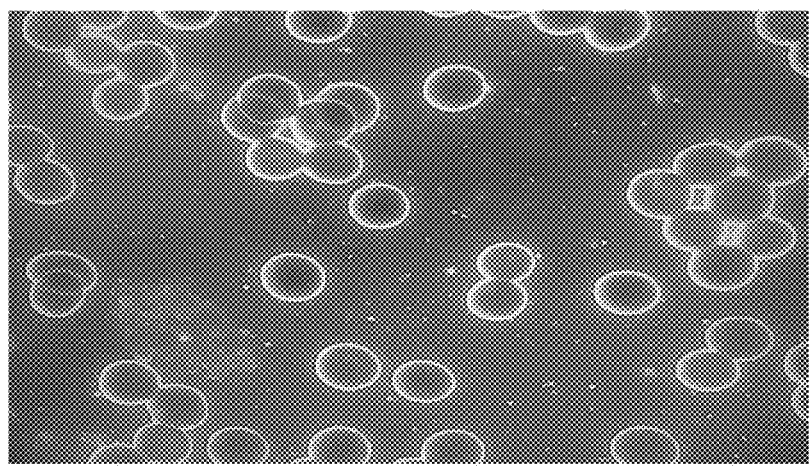
FIG. 11 is a cell graph of peripheral blood of the treatment group in Example 3.

The results are shown in FIG. 10 and FIG. 11. FIG. 10 shows the peripheral blood of the subjects in the control group, and FIG. 11 shows the peripheral blood of the subjects in the treatment group. It can be seen from FIG. 10 that cell adhesion, aggregation, rouleau formation of red cells and cell cluster embolism occur in the peripheral blood of the subjects in the control group. However, it is clear from FIG. 11 that, with the MSC preparation cultured by adding the ligustrazine hydrochloride and the Shenmai injection which are traditional Chinese medicine injections for activating blood circulation to remove blood stasis, supplementing qi and nourishing yin, the red blood cell morphology of the subjects is normal without aggregation.

From the above results, it is clear that red blood cells in the blood of the subjects are normally separated (FIG. 11) in half an hour after injection of the MSCs preparation of the invention, which is consistent with the theory of traditional Chinese medicine that "qi commands the blood and the blood carries qi". According to the traditional Chinese medicine, normal flow of qi ensures normal flow of blood while stagnation of qi causes stagnation of blood. Myocardial infarction with blood stasis and stagnation will hinder the circulation of qi. Therefore, in addition to a hydrochloride of ligustrazine which is an active ingredient of traditional Chinese medicine *Ligusticum wallichii* with the characteristics of activating blood circulation to remove blood stasis, ginseng for tonifying heart qi and the Radix Ophiopogonis preparation Shenmai injection for nourishing heart and yin blood are added to treat myocardial infarction to keep qi and blood unobstructed, and the effect is better.

II. Clinical Effect

The preparation has been applied to dozens of cases with myocardial infarction and severe lesions in three coronary arteries in Foshan. Typical cases have survived since 2001. The cases are as follows:

The 47-year-old male, Mr. Mai, was admitted to a hospital for chest tightness for seven days. Cardiography showed 80%-90% stenosis in proximal-middle segments of the left anterior descending coronary artery, and approximately 80%-90% stenosis in proximal-middle segments of the right coronary artery. The patient was diagnosed with: 1. latent coronary heart disease with lesions in three coronary arteries, and 2. hyperuricemia. The patient was advised to receive further coronary intervention, but both the patient and his family refused. The patient was later introduced to the applicant office, and given the preparation by intravenous infusion for four times at an interval of 7-15 days. The patient has survived without any symptoms and discomfort. The reexamination in Shunde Hospital of Southern Medical University in August 2018 revealed that the stenosis was improved to 60-70% stenosis in the middle segment of the right coronary artery, approximately 70-85% lumen stenosis in the proximal-middle segments of the left anterior descending coronary artery, and significant improvement in old occlusion of the distal segment of the circumflex artery.

The technical features of the above examples can be combined in any way. For brevity, not all possible combinations of the technical features of the above examples are described. However, it should be considered that the technical features are included in the scope of the specification provided that there is no contradiction in the combinations thereof.

The above examples illustrate several embodiments of the invention only, but should not be construed as limiting the scope of the invention despite of specific and detailed description. It should be noted that a person skilled in the art can make various changes and improvements without departing from the concept of the invention, which should be incorporated in the protection scope of the invention. Therefore, the scope of protection of the invention patent shall be subject to appended claims.

What is claimed is:

1. A culture method of umbilical cord mesenchymal stem cells (MSCs), comprising:
culturing primary cells obtained from Wharton's jelly of umbilical cords in a serum-free medium under hypoxic condition until a first passage (P1) to obtain P1 primary cells by subculturing the primary cells; wherein the subculturing is carried out by
preparing a single cell suspension of the primary cells collected from the culturing step and obtaining a cell pellet from the cell suspension by centrifugation and then obtaining a cell suspension from the cell pellet by adding a serum-free medium to the cell pellet to obtain the P1 primary cells;
culturing the P1 primary cells under a hypoxic condition until a second passage (P2) to obtain P2 primary cells by subculturing the P1 primary cells, and repeat the subculturing for P3 and subsequent passages; wherein ligustrazine hydrochloride and Shenmai injection are added to P3 and each subsequent subculture; and
obtaining MSCs from P3 or each subsequent subculture by isolating cells that are CD31-negative, HLA-DR-negative, CD34-negative, CD45-negative, CD44-positive, CD73-positive, CD90-positive and CD105-positive.

2. The culture method of MSCs according to claim 1, wherein the concentration of the ligustrazine hydrochloride added is 40-80 mg/L and the Shenmai injection added is 0.5% by volume.

3. The culture method of MSCs according to claim 1, wherein the hypoxic condition is provided by culturing in a carbon dioxide incubator with an oxygen concentration of 3-10%; and the serum-free medium is selected from a mesenchymal stem cell serum-free medium or a medium obtained by adding cytokines to a DMEM, F12, DMEM/F12 or RPMI1640 basal medium.

4. The culture method of MSCs according to claim 1, wherein the ligustrazine hydrochloride and the Shenmai injection are added to the subculture up to P6.

5. The culture method of MSCs according to claim 1, wherein the Wharton's Jelly is obtained from umbilical cord tissue by collecting umbilical cord tissues obtained by caesarean sections from donors, transporting the tissues under refrigeration, cleaning and stripping blood vessels in the tissues; and wherein the MSCs obtained from P3 or each subsequent subculture are tested for purity, cell growth activity, bacteria and mycoplasma, endotoxin, exogenous pathogenic factors, abnormal immune response, tumorigenicity and/or residual volume of ingredients added to the MSCs including bovine serum albumin, antibiotics, cytokines and phenol red.

6. The culture method of MSCs according to claim 2, wherein the Wharton's Jelly is obtained from umbilical cord tissue by collecting umbilical cord tissues obtained by caesarean sections from donors, transporting the tissues under refrigeration, cleaning and stripping blood vessels in the tissues; and wherein the MSCs obtained from P3 or each subsequent subculture are tested for purity, cell growth activity, bacteria and mycoplasma, endotoxin, exogenous pathogenic factors, abnormal immune response, tumorigenicity and/or residual volume of ingredients added to the MSCs including bovine serum albumin, antibiotics, cytokines and phenol red.

7. The culture method of MSCs according to claim 3, wherein the Wharton's Jelly is obtained from umbilical cord tissue by collecting umbilical cord tissues obtained by caesarean sections from donors, transporting the tissues under refrigeration, cleaning and stripping blood vessels in the tissues; and wherein the MSCs obtained from P3 or each subsequent subculture are tested for purity, cell growth activity, bacteria and mycoplasma, endotoxin, exogenous pathogenic factors, abnormal immune response, tumorigenicity and/or residual volume of ingredients added to the MSCs including bovine serum albumin, antibiotics, cytokines and phenol red.

8. The culture method of MSCs according to claim 4, wherein the Wharton's Jelly is obtained from umbilical cord tissue by collecting umbilical cord tissues obtained by caesarean sections from donors, transporting the tissues under refrigeration, cleaning and stripping blood vessels in the tissues; and wherein the MSCs obtained from P3 or each subsequent subculture are tested for purity, cell growth activity, bacteria and mycoplasma, endotoxin, exogenous pathogenic factors, abnormal immune response, tumorigenicity and/or residual volume of ingredients added to the MSCs including bovine serum albumin, antibiotics, cytokines and phenol red.

9. The culture method of MSCs according to claim 5, wherein the method further comprising:
   1) testing the donors before the collection step of the umbilical cord tissues for fulminant infectious diseases, determining donors not infected with the fulminant infectious diseases to be eligible; wherein the fulminant infectious diseases comprise HIV, hepatitis B virus, hepatitis C virus, *Treponema pallidum*, cytomegalovirus, EB virus and human T-cell lymphotropic virus;
   2) testing the donors for genetic disorders before the collection step of the umbilical cord tissues; determining the donors free of the genetic disorders to be eligible; wherein the genetic disorders are selected from the group consisting of achondroplasia, congenital deafness, vitamin D-resistant rickets, phenylketonuria, hemophilia, progressive muscular dystrophy and glucose-6-phosphate dehydrogenase deficiency; and
   3) confirming h donors have not traveled to or stayed in epidemic areas within 3 months before the collection step of the umbilical cord tissues.

10. The culture method of MSCs according to claim 6, wherein h method further comprising:
   1) testing the donors before the collection step of the umbilical cord tissues for fulminant infectious diseases, determining donors not infected with the fulminant infectious diseases to be eligible; wherein the fulminant infectious diseases comprise HIV, hepatitis B virus, hepatitis C virus, *Treponema pallidum*, cytomegalovirus, EB virus and human T-cell lymphotropic virus;
   2) testing the donors for genetic disorders before the collection step of the umbilical cord tissues; determining the donors free of the genetic disorders to be eligible; wherein the genetic disorders are selected from the group consisting of achondroplasia, congenital deafness, vitamin D-resistant rickets, phenylketonuria, hemophilia, progressive muscular dystrophy and glucose-6-phosphate dehydrogenase deficiency; and
   3) confirming the donors have not traveled to or stayed in epidemic areas within 3 months before the collection step of the umbilical cord tissues.

11. The culture method of MSCs according to claim 7, wherein the method further comprising:
   1) testing h donors before the collection step of the umbilical cord tissues for fulminant infectious diseases, determining donors not infected with the fulminant infectious diseases to be eligible; wherein the fulminant infectious diseases comprise HIV, hepatitis B virus, hepatitis C virus, *Treponema pallidum*, cytomegalovirus, EB virus and human T-cell lymphotropic virus;
   2) testing the donors for genetic disorders before the collection step of the umbilical cord tissues; determining the donors free of the genetic disorders to be eligible; wherein the genetic disorders are selected from the group consisting of achondroplasia, congenital deafness, vitamin D-resistant rickets, phenylketonuria, hemophilia, progressive muscular dystrophy and glucose-6-phosphate dehydrogenase deficiency; and
   3) confirming h donors have not traveled to or stayed in epidemic areas within 3 months before the collection step of the umbilical cord tissues.

12. The culture method of MSCs according to claim 8, wherein h method further comprising:
   1) testing the donors before the collection step of the umbilical cord tissues for fulminant infectious diseases, determining donors not infected with the fulminant infectious diseases to be eligible; wherein the fulminant infectious diseases comprise HIV, hepatitis B virus, hepatitis C virus, *Treponema pallidum*, cytomegalovirus, EB virus and human T-cell lymphotropic virus;
   2) testing the donors for genetic disorders before the collection step of the umbilical cord tissues; determining the donors free of the genetic disorders to be eligible; wherein the genetic disorders are selected from the group consisting of achondroplasia, congenital deafness, vitamin D-resistant rickets, phenylketonuria, hemophilia, progressive muscular dystrophy and glucose-6-phosphate dehydrogenase deficiency; and
   3) confirming the donors have not traveled to or stayed in epidemic areas within 3 months before the collection step of the umbilical cord tissues.

\* \* \* \* \*